United States Patent
Sasajima et al.

[11] 3,979,390
[45] Sept. 7, 1976

[54] BUTYROPHENONE DERIVATIVES AND PRODUCTION THEREOF

[75] Inventors: Kikuo Sasajima, Toyonaka; Keiichi Ono; Masaru Nakao, both of Osaka; Isamu Maruyama, Minoo; Masaharu Takayama, Toyonaka; Shigenari Katayama, Takarazuka; Junki Katsube, Toyonaka; Shigeho Inaba, Takarazuka; Hisao Yamamoto, Nishinomiya, all of Japan

[73] Assignee: Sumitomo Chemical Company, Limited, Japan

[22] Filed: Mar. 16, 1973

[21] Appl. No.: 341,858

[30] Foreign Application Priority Data
Mar. 18, 1972 Japan.............................. 47-27610

[52] U.S. Cl...................... 260/268 R; 260/268 PH; 260/289 R; 260/293.6; 260/293.66; 260/293.8
[51] Int. Cl.²...................................... C07D 295/10
[58] Field of Search...... 260/268 R, 268 PH, 289 R, 260/293.6, 293.66, 293.8

[56] References Cited
UNITED STATES PATENTS

| | | | |
|---|---|---|---|
| 3,155,669 | 11/1964 | Janssen.............. | 260/294 |
| 3,161,645 | 12/1964 | Janssen.............. | 260/293.4 |
| 3,438,991 | 4/1969 | Janssen.............. | 260/294.7 |
| 3,799,932 | 3/1974 | Yamamoto et al.... | 260/293.6 |

FOREIGN PATENTS OR APPLICATIONS

| | | | |
|---|---|---|---|
| 753,472 | 12/1970 | Belgium............ | 260/293.8 |
| 763,838 | 8/1971 | Belgium............ | 260/268 |

OTHER PUBLICATIONS
Cram et al., "Organic Chemistry", McGraw–Hill, New York (1964), p. 292.
Cram et al., "Organic Chemistry", McGraw–Hill, New York (1964), pp. 384–386.

*Primary Examiner*—G. Thomas Todd
*Attorney, Agent, or Firm*—Craig & Antonelli

[57] ABSTRACT

A process for producing butyrophenone derivatives of the formula:

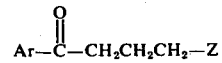

which comprises reacting a compound of the formula:

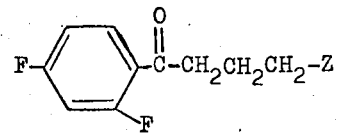

with an amine of the formula

H-W (wherein Ar represents a group of either one of the formulas:

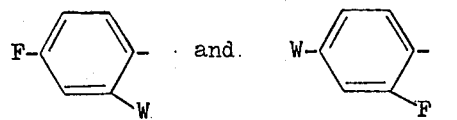

Z is a secondary amino group and W is the residue of an amine excluding a hydrogen atom therefrom). The said butyrophenone derivatives and their salts exhibit a variety of beneficial pharmacological activities including a central and autonomic nervous system depressing activity.

6 Claims, No Drawings

BUTYROPHENONE DERIVATIVES AND PRODUCTION THEREOF

The present invention is concerned with butyrophenone derivatives and production thereof, particularly pharmacologically active butyrophenone derivatives and their intermediates, and production thereof.

In one aspect of the present invention, it relates to a novel and advantageous process for producing butyrophenone derivatives of the formula:

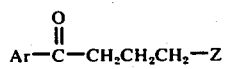
[I]

wherein Ar represents a group of either one of the formulas:

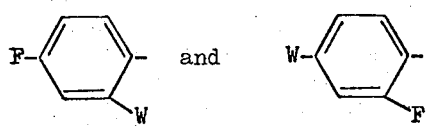

wherein W is the residue of an amine excluding a hydrogen atom therefrom) and Z is a secondary amino group of either one of the formulas:

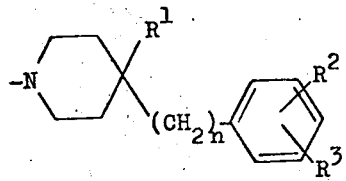

(wherein $R^1$ is hydrogen or hydroxyl, $R^2$ and $R^3$ are each hydrogen, halogen, $C_1$-$C_4$ alkyl, $C_1$-$C_4$ alkoxy or trifluoromethyl and $n$ is an integer of 0 or 1),

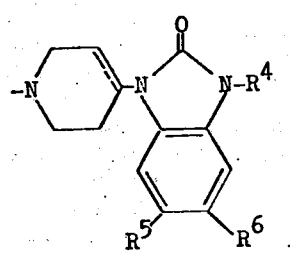

(wherein $R^4$ is hydrogen or $C_1$-$C_4$ alkyl, $R^5$ and $R^6$ are each hydrogen, halogen or $C_1$-$C_4$ alkyl and the dotted line is an optional bond between the carbon atoms at the 3- and 4-positions of the piperidine ring),

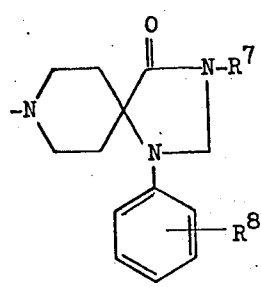

(wherein $R^7$ is hydrogen or $C_1$-$C_4$ alkyl and $R^8$ is hydrogen, halogen, $C_1$-$C_4$ alkyl or $C_1$-$C_4$ alkoxy),

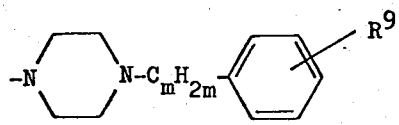

(wherein $R^9$ is hydrogen, halogen, $C_1$-$C_4$ alkyl, $C_1$-$C_4$ alkoxy or trifluoromethyl and $m$ is an integer of 0, 1 or 2), and

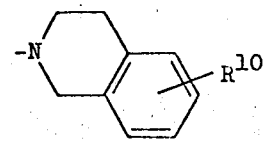

wherein $R^{10}$ is hydrogen, halogen, hydroxyl, $C_1$-$C_4$ alkyl or $C_1$-$C_4$ alkoxy).

The amine residue represented by the symbol W may be the same one as indicated by the symbol Z or the one selected from the group consisting of morpholino, pyrrolidino, piperidino and a group of the formula:

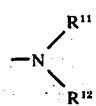

(wherein $R^{11}$ and $R^{12}$ are each hydrogen, $C_1$-$C_8$ alkyl, hydroxy-substituted $C_1$-$C_8$ alkyl, $C_1$-$C_4$ alkoxy-substituted $C_1$-$C_8$ alkyl, di($C_1$-$C_4$ alkyl)amino-substituted $C_1$-$C_8$ alkyl, $C_3$-$C_7$ cycloalkyl or optionally substituted aralkyl).

In the butyrophenone compounds of the formula, [I], there are included two kinds of the compounds of the formulas:

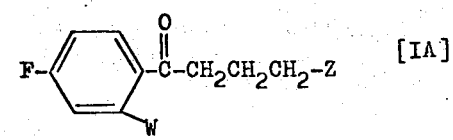
[IA]

and

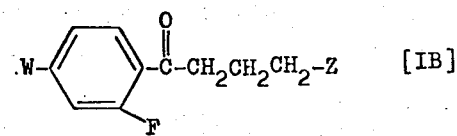
[IB]

wherein Z and W are each as defined above.

In another aspect of this invention, it relates to novel pharmacologically active butyrophenone derivatives of the formula:

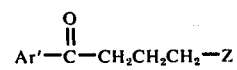
[I']

wherein Ar' represents a group of either one of the formulas:

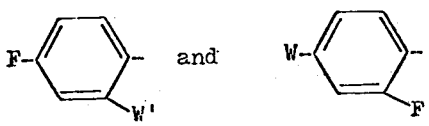

(in which W' is the residue of an amine excluding a hydrogen atom therefrom and W is as defined above) and Z is as defined above, and their acid addition salts.

The amine residue represented by the symbol W' may be the same one as indicated by the symbol W but other than amino and N-monoalkylamino.

In the butyrophenone compounds of the formula [I'], there are included two kinds of the compounds of the formulas:

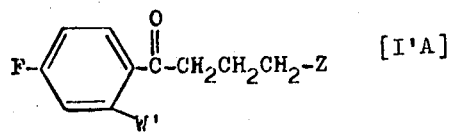

and

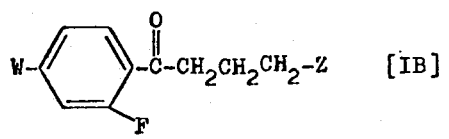

wherein Z, W and W' are each as defined above.

In a further aspect of the invention, it relates to new difluorobutyrophenone derivatives of the formula:

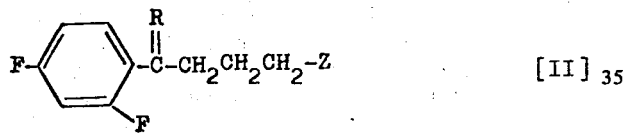

wherein R is oxygen, ethylenedioxy or ethylenedithio and Z is as defined above, and a process for preparing them.

In the difluorobutyraphenone compounds of the formula [II], there are included two kinds of the compounds of the formulas:

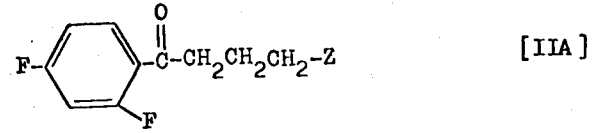

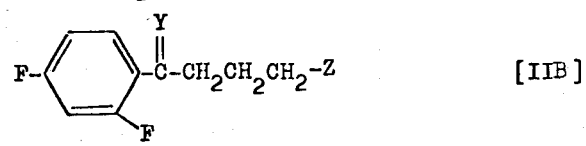

wherein Y is ethylenedioxy or ethylenedithio and Z is as defined above.

In the significances as defined above, alkyl includes methyl, ethyl, n-propyl, isopropyl, n-butyl and sec.-butyl; $C_1$-$C_4$ alkoxy includes methoxy, ethoxy, n-propoxy, isopropoxy and t-butoxy; $C_3$-$C_7$ cycloalkyl includes cyclopropyl, cyclobutyl, cyclopentyl, cyclohexyl and cycloheptyl; hydroxy-substituted $C_1$-$C_8$ alkyl includes 2-hydroxyethyl, 3-hydroxy-n-propyl, 2-hydroxy-n-propyl, 2-hydroxy-1-methylethyl, 1-hydroxymethyl-n-propyl, 2-hydroxy-1,1-dimethylethyl and 5-hydroxy-n-pentyl; $C_1$-$C_4$ alkoxy-substituted $C_1$-$C_8$ alkyl includes 2-methoxyethyl, 2-ethoxyethyl, 2-methoxy-1-methylethyl and 3-methoxy-n-propyl; dialkylamino-substituted $C_1$-$C_8$ alkyl includes 2-dimethylaminoethyl, 3-dimethylamino-n-propyl, 2-diethylaminoethyl and 4-diethylamino-1-methyl-n-butyl; halogen includes fluorine, chlorine, bromine and iodine; and aralkyl includes optionally substituted benzyl, phenethyl, benzhydryl and naphthylmethyl (e.g. benzyl, p-methoxybenzyl, p-methylbenzyl, o,p-dimethylbenzyl, p-fluorobenzyl, p-chlorobenzyl, α-ethylbenzyl, phenethyl, 3,4-dihydroxyphenethyl, benzhydryl, 1-naphthalenemethyl).

Some of the butyrophenone compounds [I], i.e. those of the formula [IA: W = amino or N-monoalkylamino], are known [cf. Belgian Patents Nos. 753,472 and 763,838].

As the results of the extensive study, it has now been found that the butyrophenone compounds [I] can be advantageously produced by the use of the diflurobutyrophenone compounds [IIA]. It has also been found that the butyrophenone compounds [I'] and [II] exhibit a variety of beneficial pharmacological and biological activities and are useful as psychotropic, tranquilizing, analgesic, antispasmodic, autonomotropic, antiinflammatory and/or antifungal agents.

Accordingly, a basic object of the present invention is to provide novel processes for producing the known and new pharmacologically active butyrophenone compounds [I]. Another object of this invention is to provide the butyrophenone compounds [I'] and the difluorobutyrophenone compounds [II], which are per se useful as medicaments. A further object of the invention is to provide the difluorobutyrophenone compounds [IIA], which are useful as intermediates in the production of the butyrophenone compounds [I]. These and other objects of the invention will be apparent to those conversant with the art to which the present invention pertains from the foregoing and subsequent descriptions.

The production of the butyrophenone compounds [I] according to the present invention is shown in the following scheme:

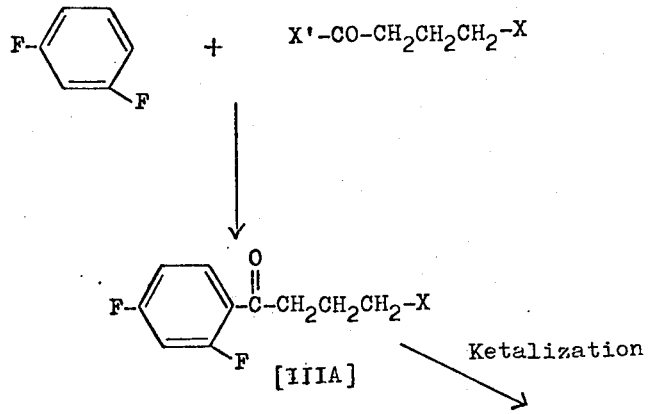

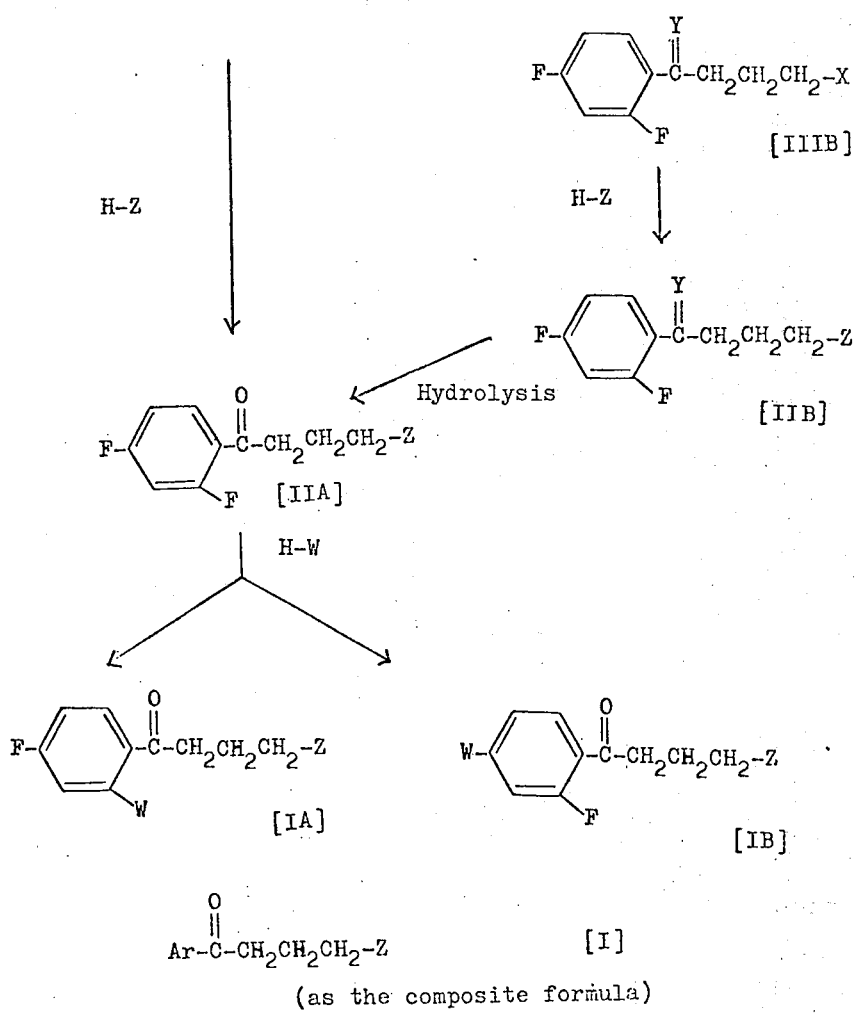

(as the composite formula)

wherein X and X' are each halogen and Ar, Z, W and Y are each as defined above.

The difluorobutyrophenone compound [IIA] can be prepared by reacting the compound [IIIA], which may be prepared by the reaction between m-difluorobenzene and a γ-halobutyryl halide, with a secondary amine of the formula: H-Z (wherein Z is as defined above) in an inert solvent.

The reaction is favorably carried out in the presence of an acid binding agent such as an inorganic base (e.g. potassium carbonate, sodium carbonate, sodium bicarbonate) or a tertiary amine (e.g. pyridine, triethylamine, dimethylaniline). Examples of the inert solvent are an amide such as dimethylformamide, dimethylacetamide and formamide, an aromatic hydrocarbon such as benzene, toluene and xylene, an alkanol such as ethanol, propanol and butanol, an alkanone such as acetone, 2-butanone and 4-methyl-2-pentanone. The reaction is usually accelerated by elevating the temperature. A small amount of a catalytic substance such as potassium iodide is also useful for acceleration of the reaction. The reaction is normally completed within a period of time from 1 to 48 hours, and a preferred reaction time is from 5 to 20 hours.

The difluorobutyrophenone compound [IIA] can be also prepared by ketalizing the compound [IIIA], reacting the resultant ketal compound [IIIB] with the secondary amine as above and then hydrolyzing the resulting akylated compound [IIB].

While the reaction between the ketal compound [IIIB] and the secondary amine may be carried out under the same condition as in the reaction between the compound [IIIA] and the secondary amine, the former can be usually conducted under a milder condition than the latter. For instance, the reaction can be accomplished at a temperature from 25° to 100°C within 3 hours.

The previous ketalization and the subsequent hydrolysis may be effected by per se conventional procedures. For instance, the ketalization is accomplished by treating the compound [IIIA] with a ketalizing agent such as ethylene glycol or ethylene dithioglycol in the presence of a dehydrative catalyst such as p-toluenesulfonic acid or conc. sulfuric acid, usually in an inert solvent (e.g. benzene, toluene, xylene) at an elevated temperature. Further, for instance, the hydrolysis is accomplished by treating the alkylated compound [IIB] with an acidic substance such as a mineral acid (e.g. hydrochloric acid, sulfuric acid, phosphoric acid), an organic acid (e.g. oxalic acid, tartaric acid) or an acidic ion exchange resin in water or an alkanol (e.g. methanol, ethanol, propanol), usually under a mild condition, e.g. at room temperature.

The thus prepared difluorobutyrophenone compound [IIA] can be readily converted into its organic or inorganic acid addition salts by a per se conventional procedure.

Examples of the difluorobutyrophenone compound [IIA] are as follows:
γ-(4-Phenylpiperidin-1-yl)-2,4-difluorobutyrophenone;
γ-(4-Hydroxy-4-phenylpiperidin-1-yl)-2,4-difluorobutyrophenone;
γ-[4-(4-Chlorophenyl)-4-hydroxypiperidin-1-yl]-2,4-difluorobutyrophenone;
γ-[4-Hydroxy-4-(3-trifluoromethylphenyl)piperidin-1-yl]-2,4-difluorobutyrophenone;
γ-[4-Hydroxy-4-(4-methylphenyl)piperidin-1-yl]-2,4-difluorobutyrophenone;
γ-[4-Hydroxy-4-(4-methoxyphenyl)piperidin-1-yl]-2,4-difluorobutyrophenone;
γ-[4-(4-Chloro-3-trifluoromethylphenyl)-4-hydroxypiperidin-1-yl]-2,4-difluorobutyrophenone;
γ-(4-Benzyl-4-hydroxypiperidin-1-yl)-2,4-difluorobutyrophenone;
γ-[4-(4-Chlorobenzyl)-4-hydroxypiperidin-1-yl]-2,4-difluorobutyrophenone;
γ-[4-(2-Oxo-1-benzimidazolinyl)piperidin-1-yl]-2,4-difluorobutyrophenone;
γ-[4-(2-Oxo-1-benzimidazolinyl)-1,2,3,6-tetrahydropyridin-1-yl]-2,4-difluorobutyrophenone;
γ-(4-Oxo-1-phenyl-1,3,8-triazaspiro[4,5]decan-8-yl)-2,4-difluorobutyrophenone;
γ-(4-Phenylpiperazin-1-yl)-2,4-difluorobutyrophenone;
γ-[4-(2-Methoxyphenyl)piperazin-1-yl)]-2,4-difluorobutyrophenone;
γ-(1,2,3,4-Tetrahydroisoquinolin-1-yl)-2,4-difluorobutyrophenone;
γ-[4-(2-Methylphenyl)piperazin-1-yl]-2,4-difluorobutyrophenone;
γ-[4-(4-Fluorophenyl)piperazin-1-yl]-2,4-difluorobutyrophenone, etc.

The difluorobutyrophenone compound [IIA] or its acid addition salt is reacted with an amine of the formula: H-W (wherein W is as defined above) to give the objective butyrophenone compound [I].

The reaction is usually carried out by treatment of the difluorobutyrophenone compound [IIA] or its acid addition salt with a not less than equimolar amount of the amine in the presence or absence of an inert solvent at room temperature or under heating.

As the result of the reaction, there are obtained the butyrophenone compounds [IA] and/or [IB]. By adoption of a suitable reaction condition, there is produced predominantly either one of the butyrophenone compounds [IA] and [IB]. Examples of the reaction conditions which may afford any influence on the selectivity of the product are such as kinds and properties of solvents and/or the amine employed, the presence or absence of solvents, the concentration of the amine, the reaction temperature and their combination. For instance, the use of a less polar solvent such as benzene, toluene, xylene, dioxane or carbon tetrachloride is favorable for the production of the butyrophenone compound [IA], while the use of a polar solvent such as water, formamide, dimethylformamide, dimethylsulfoxide, methanol or ethanol is preferred for the preparation of the butyrophenone compound [IB]. When the reaction is conducted in the absence of any solvent, the selectivity of the position to be substituted mainly depends on the kind of the amine employed. Thus, it is possible to yield selectively the butyrophenone compound [IA] or [IB] as a main product, often as a sole product.

The butyrophenone compounds [IA] and/or [IB] thus produced can be readily separated from the reaction mixture by a per se conventional procedure. When the product is a mixture of the butyrophenone compounds [IA] and [IB], each component can be isolated also by a conventional procedure such as recrystalization or column chromatography.

When the product is a butyrophenone compound of the formula:

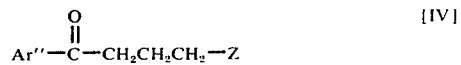

$$Ar''-\overset{O}{\underset{\|}{C}}-CH_2CH_2CH_2-Z \qquad [IV]$$

wherein Ar'' represents a group of either one of the formulas:

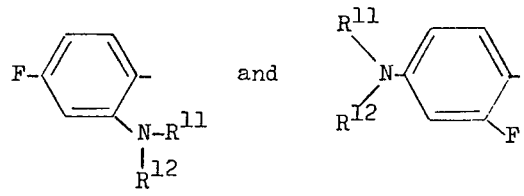

(wherein $R^{11}$ and $R^{12}$ are each as defined above but at least one of them represents an optionally substituted benzyl group) and Z is as defined above, i.e. either one of the compounds of the formulas:

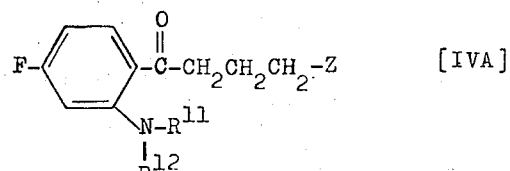

[IVA]

and

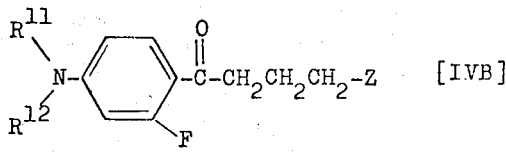

[IVB]

wherein R¹¹, R¹² and Z are each as defined above, it can be converted into the corresponding debenzylated compound of the formula:

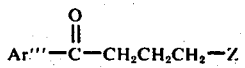  [V]

wherein Ar''' represents a group of either one of the formulas:

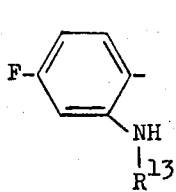 and 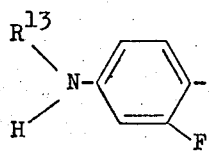

(wherein $R^{13}$ is hydrogen, $C_1$-$C_8$ alkyl, hydroxy-substituted $C_1$-$C_8$ alkyl, $C_1$-$C_4$ alkoxy-substituted $C_1$-$C_8$ alkyl, di($C_1$-$C_4$ alkyl)-amino-substituted $C_1$-$C_8$ alkyl or $C_3$-$C_7$ cycloalkyl) and Z is as defined above, i.e. either one of the compounds of the formulas:

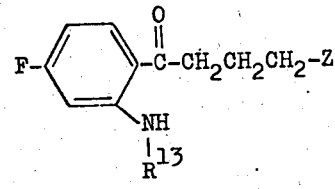 [VA]

and

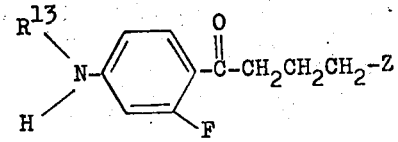 [VB]

wherein $R^{13}$ and Z are each as defined above, by hydrogenating the former by a per se conventional procedure.

Thus, the hydrogenation may be conducted in the presence of a catalyst such as a metal (e.g. palladium, platinum, rhodium, nickel) or its oxide or hydroxide, optionally supported on a carrier in an inert solvent (e.g. water, methanol, ethanol, ether, tetrahydrofuran, dioxane, benzene, toluene, xylene). A peferred catalyst is palladium on charcoal. A favorable solvent is an alkanol such as methanol, ethanol or propanol. The hydrogenation proceeds readily at room temperature under a hydrogen pressure of 1 to 5 atm., while a higher temperature and a higher pressure may be also adopted. The butyrophenone compound [IV] is usually subjected to hydrogenation in the form of the acid addition salt and, in case of the free base being used, the addition of an acid to the reaction system is desired.

The recovery of the butyrophenone compound [V] thus produced from the reaction mixture may be effected by a conventional procedure.

When the butyrophenone compound [I] (or the butyrophenone compound [V]) is obtained in the form of a free base, it may be converted into its acid addition salt by a conventional procedure. Examples of such acid addition salt include pharmaceutically acceptable ones such as hydrochloride, hydrobromide, sulfate, phosphate, sulfamate, citrate, oxalate, lactate, maleate, malate, succinate, tartrate, cinnamate, acetate, benzoate, gluconate, ascorbate, etc.

Examples of the butyrophenone compound [I] are as follows:

γ-(4-Hydroxy-4-phenylpiperidin-1-yl)-4-amino-2-fluorobutyrophenone;
γ-[4-(4-Chlorophenyl)-4-hydroxypiperidin-1-yl]-4-amino-2-fluorobutyrophenone;
γ-[4-Hydroxy-4-(3-trifluoromethylphenyl)piperidin-1-yl]-4-amino-2-fluorobutyrophenone;
γ-[4-Hydroxy-4-(4-methylphenyl)piperidin-1-yl]-4-amino-2-fluorobutyrophenone;
γ-[4-Hydroxy-4-(4-methoxyphenyl)piperidin-1-yl]-4-amino-2-fluorobutyrophenone;
γ-[4-(4-Chloro-3-trifluoromethylphenyl)-4-hydroxypiperidin-1-yl]-4-amino-2-fluorobutyrophenone;
γ-(4-Benzyl-4-hydroxypiperidin-1-yl)-4-amino-2-fluorobutyrophenone;
γ-[4-(4-chlorobenzyl)-4-hydroxypiperidin-1-yl]-4-amino-2-fluorobutyrophenone;
γ-[4-(2-Oxo-1-benzimidazolinyl)piperidin-1-yl]-4-amino-2-fluorobutyrophenone;
γ-(4-Oxo-1-phenyl-1,3,8-triazaspiro[4,5]decan-8-yl)-4-amino-2-fluorobutyrophenone;
γ-(4-Oxo-1-phenyl-1,3,8-triazaspiro[4,5]decan-8-yl)-2-amino-4-fluorobutyrophenone;
γ-(4-Phenylpiperazin-1-yl)-4-amino-2-fluorobutyrophenone;
γ-[4-(2-Methoxyphenyl)piperazin-1-yl]-4-amino-2-fluorobutyrophenone;
γ-[1,2,3,4-Tetrahydroisoquinolin-2-yl]-4-amino-2-fluorobutyrophenone;
γ-[4-Hydroxy-4-(3-trifluoromethylphenyl)piperidin-1-yl]-2-fluoro-4-methylaminobutyrophenone;
γ-(4-Oxo-1-phenyl-1,3,8-triazaspiro[4,5]decan-8-yl)-2-fluoro-4-methylaminobutyrophenone;
γ-(4-Oxo-1-phenyl-1,3,8-triazaspiro[4,5]decan-8-yl)-4-fluoro-2-methylaminobutyrophenone;

γ-(4-Phenylpiperazin-1-yl)-2-fluoro-4-methylaminobutyrophenone;
γ-[4-Hydroxy-4-(3-trifluoromethylphenyl)piperidin-1-yl]-4-ethylamino-2-fluorobutyrophenone;
γ-[4-(4-Chloro-3-trifluoromethylphenyl)-4-hydroxypiperidin-1-yl]-4-ethylamino-2-fluorobutyrophenone;
γ-(4-Oxo-1-phenyl-1,3,8-triazaspiro[4,5]decan-8-yl)-4-ethylamino-2-fluorobutyrophenone;
γ-[4-(2-Oxo-1-benzimidazolinyl)piperidin-1-yl]-4-ethylamino-2-fluorobutyrophenone;
γ-(4-Phenylpiperazin-1-yl)-4-ethylamino-2-fluorobutyrophenone;
γ-[4-Hydroxy-4-(3-trifluoromethylphenyl)piperidin-1-yl]-2-ethylamino-4-fluorobutyrophenone;
γ-[4-(4-Chloro-3-trifluoromethylphenyl)-4-hydroxypiperidin-1-yl]-2-ethylamino-4-fluorobutyrophenone;
γ-[4-(2-Methoxyphenyl)piperazin-1-yl]-2-ethylamino-4-fluorobutyrophenone;
γ-[4-Hydroxy-4-(3-trifluoromethylphenyl)piperidin-1-yl]-2-fluoro-4-n-propylaminobutyrophenone;
γ-(4-Oxo-1-phenyl-1,3,8-triazaspiro[4,5]decan-8-yl)-2-fluoro-4-n-propylaminobutyrophenone;
γ-[4-Hydroxy-4-(3-trifluoromethylphenyl)piperidin-1-yl]-2-fluoro-4-isopropylaminobutyrophenone;
γ-(4-Oxo-1-phenyl-1,3,8-triazaspiro[4,5]decan-8-yl)2-fluoro-4-isopropylbutyrophenone;
γ-(4-Oxo-1-phenyl-1,3,8-triazaspiro[4,5]decan-8-yl)-4-fluoro-2-n-propylaminobutyrophenone;
γ-(4-Oxo-1-phenyl-1,3,8-triazaspiro[4,5]decan-8-yl)-4-fluoro-2-isopropylaminobutyrophenone;
γ-[4-Hydroxy-4-(3-trifluoromethylphenyl)piperidin-1-yl]-4-fluoro-2-isopropylaminobutyrophenone;
γ-[4-Hydroxy-4-(3-trifluoromethylphenyl)piperidin-1-yl]-4-n-butylamino-2-fluorobutyrophenone;
γ-[4-Hydroxy-4-(3-trifluoromethylphenyl)-piperidin-1-yl]-4-sec-butylamino-2-fluorobutyrophenone;
γ-[4-Hydroxy-4-(3-trifluoromethylphenyl)piperidin-1-yl]-4-t-butylamino-2-fluorobutyrophenone;
γ-[4-Hydroxy-4-(3-trifluoromethylphenyl)piperidin-1-yl]-4-cyclopropylmethylamino-2-fluorobutyrophenone;
γ-(4-Oxo-1-phenyl-1,3,8-triazaspiro[4,5]decan-8-yl-4-sec-butylamino-2-fluorobutyrophenone;
γ-(4-Oxo-1-phenyl-1,3,8-triazaspiro[4,5]decan-8-yl-4-t-butylamino-2-fluorobutyrophenone;
γ-[4-(2-Methoxyphenylpiperazin-1-yl]-4-sec.-butylamino-2-fluorobutyrophenone;
γ-(4-Oxo-1-phenyl-1,3,8-triazaspiro[4,5]decan-8-yl)-2-n-butylamino-4-fluorobutyrophenone;
γ-(4-Oxo-1-phenyl-1,3,8-triazaspiro[3,5]decan-8-yl)-2-sec-butylamino-4-fluorobutyrophenone;
γ-[4-Hydroxy-4-(3-trifluoromethylphenyl)piperidin-1-yl]-2-fluoro-4-octylaminobutyrophenone;
γ-(4-Oxo-1-phenyl-1,3,8-triazaspiro-[4,5]decan-8-yl)-2-octylamino-4-fluorobutyrophenone;
γ-[4-(4-Chloro-3-trifluoromethylphenyl)-4-hydroxypiperidin-1-yl]-2-dimethylamino-4-fluorobutyrophenone;
γ-[4-(4-Chloro-3-trifluoromethylphenyl)-4-hydroxypiperidin-1-yl]-4-dimethylamino-2-fluorobutyrophenone;
γ-[4-(2-Oxo-1-benzimidazolinyl)piperidin-1-yl]-2-dimethylamino-4-fluorobutyrophenone;
γ-[4-(2-Methoxypiperazin-1-yl)-2-dimethylamino]-4-fluorobutyrophenone;
γ-(4-Phenylpiperazin-1-yl)-4-dimethylamino-2-fluorobutyrophenone;
γ-[4-(2-Oxo-1-benzimidazolinyl)piperidine-1-yl]-4-dimethylamino-2-fluorobutyrophenone;
γ-(4-Oxo-1-phenyl-1,3,8-triazaspiro[4,5]decan-8-yl)-2-diethylamino-4-fluorobutyrophenone;
γ-[4-Hydroxy-4-(3-trifluoromethylphenyl)piperidin-1-yl]-2-diethylamino-4-fluorobutyrophenone;
γ-[4-(4-Chloro-3-trifluoromethylphenyl)-4-hydroxypiperidin-1-yl]-2-diethylamino-4-fluorobutyrophenone;
γ-(4-Oxo-1-phenyl-1,3,8-triazaspiro[4,5]decan-8-yl)-2-diisopropylamino-4-fluorobutyrophenone;
γ-[4-Hydroxy-4-(3-trifluoromethylphenyl)piperidin-1-yl]-2-diisopropylamino-4-fluorobutyrophenone;
γ-(4-Oxo-1-phenyl-1,3,8-triazaspiro[4,5]decan-8-yl)-4-diisopropylamino-2-fluorobutyrophenone;
γ-(4-Oxo-1-phenyl-1,3,8-triazaspiro[4,5]decan-8-yl)-4-diisobutylamino-2-fluorobutyrophenone;
γ-[4-(2-Methoxyphenyl)piperazin-1-yl]-4-diisopropylamino-2-fluorobutyrophenone;
γ-(4-Oxo-1-phenyl-1,3,8-triazaspiro[4,5]decan-8-yl)-2-cyclopropylamino-4-fluorobutyrophenone;
γ-[4-Hydroxy-4-(3-trifluoromethylphenyl)piperidin-1-yl]-2-cyclohexylamino-4-fluorobutyrophenone;
γ-(4-Oxo-1-phenyl-1,3,8-triazaspiro[4,5]decan-8-yl)-4-cyclopropylamino-4-fluorobutyrophenone;
γ-(4-Phenylpiperazin-1-yl)-4-cyclopropylamino-2-fluorobutyrophenone;
γ-[4-Hydroxy-4-(3-trifluoromethylphenyl)piperidin-1-yl]-2-cyclohexylamino-4-fluorobutyrophenone;
γ-(4-Oxo--phenyl-1,3,8-triazaspiro[4,5]decan-8-yl)-4-cyclohexylamino-2-fluorobutyrophenone;
γ-(4-Phenylpiperazin-1-yl)-4-cycloheptylamino-2-fluorobutyrophenone;
γ-(4-Oxo-1-phenyl-1,3,8-triazaspiro[4,5]decan-8-yl)-4-fluoro-2-(2-hydroxyethylamino)butyrophenone;
γ-(4-Oxo-1-phenyl-1,3,8-triazaspiro[4,5]decan-8-yl)-4-fluoro-2-(2-hydroxy-n-propylamino)-butyrophenone;
γ-(4-Oxo-1-phenyl-1,3,8-triazaspiro[4,5]decan-8-yl)-4-fluoro-2-(2-hydroxy-1-methylethylamino)-butyrophenone;
γ-(4-Oxo-1-phenyl-1,3,8-triazaspiro[4,5]decan-8-yl)-2-fluoro-4-(1-hydroxymethyl-n-propylamino)-butyrophenone;
γ-[4-Hydroxy-4-(3-trifluoromethylphenyl)piperidin-1-yl]-4-fluoro-2-(3-hydroxypropylamino)-butyrophenone;
γ-[4-Hydroxy-4-(3-trifluoromethylphenyl)piperidin-1-yl]-4-[bis(2-hydroxyethyl)amino]-2-fluorobutyrophenone;
γ-(4-Oxo-1-phenyl-1,3,8-triazaspiro[4,5]decan-8yl)-4-fluoro-2-(2-methoxyethylamino)butyrophenone;
γ-(4-Oxo-1-phenyl-1,3,8-triazaspiro[4,5]decan-8-yl)-4-fluoro-2-(3-methoxypropylamino)-butyrophenone;
γ-(4-Oxo-1-phenyl-1,3,8-triazaspiro[4,5]decan-8-yl)-2-fluoro-4-(2-methoxy-1-methylethylamino)-butyrophenone;
γ-(4-Oxo-1-phenyl-1,3,8-triazaspiro[4,5]decan-8-yl)-2-[bis(2-ethoxyethyl)amino]-4-fluorobutyrophenone;
γ-[4-Hydroxy-4-(3-trifluoromethylphenyl)piperidin-1-yl]-4-(2-ethoxyethylamino)-2-fluorobutyrophenone;
γ-[4-Hydroxy-4-(3-trifluoromethylphenyl)piperidin-1-yl]-2-[bis(2-ethoxyethyl)amino]-4-fluorobutyrophenone;
γ-(4-Phenylpiperazin-1-yl)-2-fluoro-4-(2-methoxy-1-methylethylamino)butyrophenone;
γ-(4-Oxo-1-phenyl-1,3,8-triazaspiro[4,5]decan-8-yl)-2-(2-dimethylaminoethylamino)-4-fluorobutyrophenone;
γ-(4-Oxo-1-phenyl-1,3,8-triazaspiro[4,5]decan-8-yl)-2-(3-dimethylamino-n-propylamino)-4-fluorobutyrophenone;
γ-[4-Hydroxy-4-(3-trifluoromethylphenyl)piperidin-1-yl]-2-(3-dimethylamino-n-propylamino)-4-fluorobutyrophenone;
γ-[4-Hydroxy-4-(3-trifluoromethylphenyl)piperidin-1-yl]-4-(4-diethylamino-1-methyl-n-butylamino)-2-fluorobutyrophenone;
γ-[4-(2-Oxo-1-benzimidazolinyl)piperidin-1-yl]-2-(3-dimethylaminopropylamino)-4-fluorobutyrophenone;
γ-(4-Phenylpiperazin-1-yl)-4-(3-dimethylamino-n-propylamino)-2-fluorobutyrophenone;
γ-[4-Hydroxy-4-(3-trifluoromethylphenyl)piperidin-1-yl]-4-fluoro-2-piperidinobutyrophenone;
γ-[4-Hydroxy-4-(3-trifluoromethylphenyl)piperidin-1-yl]-4-fluoro-2-morpholinobutyrophenone;
γ-[4-Hydroxy-4-(3-trifluoromethylphenyl)piperidin-1-yl]-4-fluoro-2-(4-phenylpiperazin-1-yl)butyrophenone;
γ-[4-Hydroxy-4-(3-trifluoromethylphenyl)piperidin-1-yl]-2-fluoro-4-pyrrolidinobutyrophenone;
γ-(4-Oxo-1-phenyl-1,3,8-triazaspiro[4,5]decan-8-yl)-4-[4-(4-chlorophenyl)-4-hydroxypiperidin-1-yl]-2-fluorobutyrophenone;
γ-(4-Oxo-1-phenyl-1,3,8-triazaspiro[4,5]decan-8-yl)-2-fluoro-4-[4-hydroxy-4-(3-trifluoromethylphenyl)piperidin-1-yl]butyrophenone;
γ,4-Bis(4-oxo-1-phenyl-1,3,8-triazaspiro[4,5]decan-8-yl)-2-fluorobutyrophenone;
γ,4-Bis(4-phenylpiperazin-1-yl)-2-fluorobutyrophenone;
γ-[4-(2-Oxo-1-benzimidazolinyl)piperidin-1-yl]-4-[4-(4-chlorophenyl)-4-hydroxypiperidin-1yl]-2-fluorobutyrophenone;
γ-[4-Hydroxy-4-(3-trifluoromethylphenyl)piperidin-1-yl]-2-fluoro-4-[4-(2-oxo-1-benzimidazolinyl)-piperidin-1-yl]-butyrophenone;
γ-[4-hydroxy-4-(3-trifluoromethylphenyl)piperidin-1-yl]-2-fluoro-4-(1,2,3,4-tetrahydroisoquinolin-2-yl)butyrophenone;
γ-[4-Hydroxy-4-(3-trifluoromethylphenyl)piperidin-1-yl]-2-fluoro-2-(4-oxo-1-phenyl-1,3,8-triazaspiro[4,5]decan-8-yl)butyrophenone;
γ,4-Bis[4-hydroxy-4-(3-trifluoromethylphenyl)-piperidin-1-yl]-2-fluorobutyrophenone;
γ-[4-Hydroxy-4-(3-trifluoromethylphenyl)piperidin-1-yl]-2-fluoro-4-[4-(2-methoxyphenyl)piperazin-1-yl]butyrophenone;
γ-(4-Oxo-1-phenyl-1,3,8-triazaspiro[4,5]decan-8-yl)-2-benzylamino-4-fluorobutyrophenone;
γ-[4-(2-Oxo-1-benzimidazolinyl)piperidin-1-yl]-2-benzylamino-4-fluorobutyrophenone;
γ-[4-(2-Methoxyphenyl)piperazin-1-yl]-2-benzylamino-4-fluorobutyrophenone;
γ-(4-Oxo-1-phenyl-1,3,8-triazaspiro[4,5]decan-8-yl)-4-benzylamino-2-fluorobutyrophenone;
γ-[4-(4-Chloro-3-trifluoromethylphenyl)-4-hydroxypiperidin-1-yl]-2-benzylamino-4-fluorobutyrophenone;
γ-[4-(4-Chlorophenyl)-4-hydroxypiperidin-1-yl]-4-fluoro-2-(4-methoxybenzylamino)butyrophenone;
γ-[4-Hydroxy-4-(3-trifluoromethylphenyl)piperidin-1-yl]-4-fluoro-2-(4-methoxybenzylamino)-butyrophenone;
γ-[4-Hydroxy-4-(3-trifluoromethylphenyl)piperidin-1-yl]-2-(4-chlorobenzylamino)-4-fluorobutyrophenone;
γ-[4-Hydroxy-4-(3-trifluoromethylphenyl)piperidin-1-yl]-2-(4-fluorobenzylamino)-4-fluorobutyrophenone;
γ-[4-Hydroxy-4-(3-trifluoromethylphenyl)piperidin-1-yl]-4-fluoro-2-(4-methylbenzylamino)-butyrophenone;
γ-[4-Hydroxy-4-(3-trifluoromethylphenyl)piperidin-1-yl]-2-dibenzylamino-4-fluorobutyrophenone;
γ-(4-Oxo-1-phenyl-1,3,8-triazaspiro[4,5]decan-8-yl)-4-fluoro-2-(4-methoxybenzylamino)-butyrophenone;
γ-[4-Hydroxy-4-(3-trifluoromethylphenyl)piperidin-1-yl]-2-fluoro-4-phenethylaminobutyrophenone;
γ-[4-Hydroxy-4-(3-trifluoromethylphenyl)piperidin-1-yl]-2-fluoro-4-(N-methylbenzylamino)-butyrophenone;
γ-[4-Hydroxy-4-(3-trifluoromethylphenyl)piperidin-1-yl]-2-fluoro-4-(α,3,4-trihydroxyphenethylamino)butyrophenone, etc.

The animal tests revealed that the butyrophenone compounds [I] and [II] have pharmacological activities. Particularly, the compound [I'] and [II] show a variety of depressing properties on the central and autonomic nervous system. They exhibit beneficial pharmacological activities such as psychotropic, tranquilizing, analgesic, antispasmodic, antiinflammatory, autonomotropic and/or antifungal activities.

Each of these compounds may be brought ino a form suitable for administration according to a method known per se. For the preparation of pharmaceutical compositions, they may be mixed with carriers, diluents, lubricants, fillers and/or binders such as lactose, sucrose, calcium phosphate, starch, talcum, casein, magnesium stearate, methyl cellulose, polyglycols, tragacanth and the like, sometimes together with stabilizers and emulsifying agents. The resulting mixture may be processed in a usual manner to tablets, capsules, pills, ampoules and the like.

The following examples illustrate the present invention in more details but do not limit its scope.

Preparation of the starting materials

A. To a mixture of aluminum chloride (340 g) and carbon disulfide (1 liter) were added 114 g of m-difluorobenzene under cooling. A solution of γ-chlorobutyryl chloride (142.5 g) in carbon disulfide (200 ml) was then added dropwise to the reaction mixture at a temperature below 15°C. The resulting mixture was gradually heated until refluxing occurred and then heated under continuous refluxing for 2 hours. After cooling, the reaction mixture was poured into water (3 liters) and extracted with dichloromethane. The extract was washed with water, a diluted aqueous solution of sodium hydroxide and a saturated aqueous solution of sodium chloride in order, dried over anhydrous sodium sulfate and concentrated to give a residual oil. Vacuum distillation of the oil gave pure γ-chloro-2,4-difluorobutyrophenone. B.P. 97° –

111°C (1.0 – 1.5 mmHg). $n_D^{26}$ 1.507.

B. While a mixture of γ-chloro-2,4-difluorobutyrophenone (102.3 g), ethylene glycol (58.1 g), p-toluenesulfonic acid hydrate (3.2 g) and benzene (500 g) was heated under refluxing for 30 hours, the water produced was eliminated as an azeotropic mixture. After cooling, the reaction mixture was washed with water and dried over anhydrous sodium sulfate. The benzene layer was concentrated to give a residual oil. Vacuum distillation of the oil gave pure 4-chloro-1-(2,4-difluorophenyl)-1,1-ethylenedioxybutane. B.P. 109° – 120°C (1.3 – 1.5 mmHg). $n_D^{27}$ 1.495.

EXAMPLE 1

A mixture of γ-chloro-2,4-difluorobutyrophenone (14.2 g), 4-(4-chlorophenyl)-4-hydroxypiperidine (13.8 g), anhydrous potassium carbonate (9.0 g), potassium iodide (0.5 g) and dimethylformamide (170 ml) was heated for 20 hours at 90° – 110°C. After cooling, the reaction mixture was diluted with water and extracted with ether. The ethereal extract was sufficiently washed with water, dried over anhydrous sodium sulfate, treated with hydrogen chloride and then concentrated. Trituration and recrystallization of the residue from methanol gave γ-[4-(4-chlorophenyl)-4-hydroxypiperidin-1-yl]-2,4-difluorobutyrophenone hydrochloride. M.P. 245°C (decomposition).

EXAMPLE 2

A mixture of 4-chloro-1-(2,4-difluorophenyl)-1,1-ethylenedioxybutane (5.3 g), 4-oxo-1-phenyl-1,3,8-triazaspiro[4,5]decane (4.6 g), anhydrous potassium carbonate (0.1 g) and dimethylformamide (58 ml) was heated under refluxing for 2.5 hours. After cooling, the reaction mixture was poured into cold water (400 ml) with vigorous stirring, and the precipitate was collected and washed with water to yield 4-(4-oxo-1-phenyl-1,3,8-triazaspiro[4,5]decan-8-yl)-1-(2,4-difluorophenyl)-1,1-ethylenedioxybutane. M.P. 58° – 62°C.

EXAMPLE 3

A mixture of 4-(4-oxo-1-phenyl-1,3,8-triazaspiro[4,5]-decan-8-yl)-1-(2,4-difluorophenyl)-1,1-ethylenedioxybutane (2.0 g), methanol (29 ml), 35 % hydrochloric acid (4.7 ml) and water (10 ml) was heated under refluxing for 30 minutes. After cooling, the reaction mixture was diluted with water, made alkaline with a saturated aqueous solution of sodium carbonate and extracted with chloroform. The extract was washed with water, dried over anhydrous sodium sulfate and concentrated in vacuo. The residue was recrystallized from ethanol to yield γ-(4-oxo-1-phenyl-1,3,8-triazaspiro[4,5]decan-8-yl)-2,4-difluorobutyrophenone. M.P. 190° – 204°C.

EXAMPLE 4

In the same manner as in Examples 1 to 3, the following compounds were obtained:

4-[4-Hydroxy-4-(3-trifluoromethylphenyl)piperidin-1-yl]-1-(2,4-difluorophenyl)-1,1-ethylenedioxybutane;
γ-[4-Hydroxy-4-(3-trifluoromethylphenyl)piperidin-1-yl]-2,4-difluorobutyrophenone, M.P. 90° – 93°C; hydrochloride, M.P. 235° – 238°C;
4-[4-(p-Chlorophenyl)-4-hydroxypiperidin-1-yl]-1-(2,4-difluorophenyl)-1,1-ethylenedioxybutane;
4-[4-(2-Oxo-1-benzimidazolinyl)piperidin-1-yl]-1-(2,4-difluorophenyl)-1,1-ethylenedioxybutane;
γ-[4-(2-Oxo-1-benzimidazolinyl)piperidin-1-yl]-2,4-difluorobutyrophenone; hydrochloride, M.P. 160° – 165°C;
4-(4-Phenylpiperazin-1-yl)-1-(2,4-difluorophenyl)-1,1-ethylenedioxybutane;
γ-(4-Phenylpiperazin-1-yl)-2,4-difluorobutyrophenone; dihydrochloride, M.P. 219° – 225°C (decomposition);
4-[4-(2-Methoxyphenyl)piperazin-1-yl]-1-(2,4-difluorophenyl)-1,1-ethylenedioxybutane;
γ-[4-(2-Methoxyphenyl)piperazin-1-yl]-2,4-difluorobutyrophenone dihydrochloride, M.P. 206° – 208°C;
4-(1,2,3,4-Tetrahydroisoquinolin-2-yl)-1-(2,4-difluorophenyl)-1,1-ethylenedioxybutane;
γ-(1,2,3,4-Tetrahydroisoquinolin-2-yl)-2,4-difluorobutyrophenone; hydrochloride, M.P. 205° – 208°C;
4-[4-(4-Chloro-3-trifluoromethylphenyl)-4-hydroxypiperidin-1-yl]-1-(2,4-difluorophenyl)-1,1-ethylenedioxybutane;
γ-[4-(4-Chloro-3-trifluoromethylphenyl)-4-hydroxypiperidin-1-yl]-2,4-difluorobutyrophenone; hydrochloride, M.P. 226°C (decomposition);
4-[4-(4-Chlorobenzyl)-4-hydroxypiperidin-1-yl]-1-(2,4-difluorophenyl)-1,1-ethylenedioxybutane;
γ-[4-(4-Chlorobenzyl)-4-hydroxypiperidin-1-yl]-2,4-difluorobutyrophenone; hydrochloride, M.P. 183° – 184°C, etc.

EXAMPLE 5

A mixture of γ-[4-(4-chlorophenyl)-4-hydroxypiperidin-1-yl]-2,4-difluorobutyrophenone hydrochloride (4.0 g) and benzylamine (50 ml) was stirred at room temperature for about 30 hours. The mixture was poured into water and extracted with ethyl acetate. The extract was sufficiently washed with water and concentrated under reduced pressure. Triturating the residue with a mixture of ether and n-hexane, there was obtained γ-[4-(4-chlorophenyl)-4-hydroxypiperidin-1-yl]-2-benzylamino-4-fluorobutyrophenone. M.P. 113° – 117°C. IR $\nu_{max}^{Nujol}$ 3350, 3300, 1639, 1600 cm$^{-1}$.

EXAMPLE 6

A mixture of γ-[4-(4-chlorophenyl)-4-hydroxypiperidin-1-yl]-2,4-difluorobutyrophenone hydrochloride (4.0 g), benzylamine (20.0 g) and dimethylsulfoxide (100 ml) was stirred at 70° to 80°C for 8 hours. After cooling, the reaction mixture was poured into water and extracted with ethyl acetate. The extract was sufficiently washed with water, dried over anhydrous sodium sulfate and concentrated under reduced pressure. Treatment of the residue with ethanol afforded γ-[4-(4-chlorophenyl)-4-hydroxypiperidin-1-yl]-4-benzylamino-2-fluorobutyrophenone. M.P. 158° – 165°C. IR $\nu_{max}^{Nujol}$ 3350, 1650 cm$^{-1}$.

EXAMPLE 7

In the same manner as in Examples 5 and 6, the following compounds were obtained:

γ-[4-Hydroxy-4-(3-trifluoromethylphenyl)piperidin-1-yl]-2-benzylamino-4-fluorobutyrophenone, M.P. 80° – 82°C;
γ-[4-Hydroxy-4-(3-trifluoromethylphenyl)piperidin-1-yl]-4-benzylamino-2-fluorobutyrophenone, M.P. 122° – 125°C;
γ-(4-Oxo-1-phenyl-1,3,8-triazaspiro[4,5]decan-8-yl)-2-benzylamino-4-fluorobutyrophenone, M.P.

204° – 209°C;
γ-(4-Oxo-1-phenyl-1,3,8-triazaspiro[4,5]decan-8-yl)-4-benzylamino-2-fluorobutyrophenone;
γ-[4-Hydroxy-4-(3-trifluoromethylphenyl)piperidin-1-yl]-4-fluoro-2-(4-methoxybenzylamino)-butyrophenone;
γ-[4-Hydroxy-4-(3-trifluoromethylphenyl)piperidin-1-yl]-2-fluoro-4-(4-methoxybenzylamino)-butyrophenone, etc.

EXAMPLE 8

To a suspension of γ-[4-(p-chlorophenyl)-4-hydroxypiperidin-1-yl]-2,4-difluorobutyrophenone hydrochloride (2.0 g) in benzene (160 ml) were added 80 g of 40 % aqueous solution of dimethylamine, and the resulting mixture was stirred at room temperature for 27 hours. The benzene layer was separated, washed with water, dried over anhydrous sodium sulfate and concentrated under reduced pressure. The residue was sufficiently triturated and washed with n-hexane to afford γ-[4-(p-chlorophenyl)-4-hydroxypiperidin-1-yl]-2-dimethylamino-4-fluorobutyrophenone. M.P. 83° – 85°C.

EXAMPLE 9

A mixture of γ-[4-(p-chlorophenyl)-4-hydroxypiperidin-1-yl]-2,4-difluorobutyrophenone hydrochloride (2.0 g), 40 % aqueous solution of dimethylamine (10.0 g) and dimethylsulfoxide (30 ml) was stirred at room temperature for 1 hour. The reaction mixture was poured into cold water (200 ml). The precipitate was filtered and recrystallized from aqueous ethanol to yield γ-[4-(p-chlorophenyl)-4-hydroxypiperidin-1-yl]-4-dimethylamino-2-fluorobutyrophenone. M.P. 160° to 163°C.

EXAMPLE 10

In the same manner as in Examples 8 and 9, the following compounds were obtained:
γ-[4-(4-Chlorophenyl)-4-hydroxypiperidin-1-yl]-2-ethylamino-4-fluorobutyrophenone, M.P. 112° – 117°C;
γ-(4-Oxo-1-phenyl-1,3,8-triazaspiro[4,5]decan-8-yl)-2-ethylamino-4-fluorobutyrophenone, M.P. 169° – 176°C;
γ-(4-Oxo-1-phenyl-1,3,8-triazaspiro[4,5]decan-8-yl)-2-dimethylamino-4-fluorobutyrophenone, M.P. 93° – 106°C;
γ-[4-(4-Chlorophenyl)-4-hydroxypiperidin-1-yl]-2-fluoro-4-methylaminobutyrophenone, M.P. 132° – 137°C;
γ-[4-(4-Chlorophenyl)-4-hydroxypiperidin-1-yl]-4-ethylamino-2-fluorobutyrophenone, M.P. 137° – 140°C;
γ-(4-Oxo-1-phenyl-1,3,8-triazaspiro[4,5]decan-8-yl)-4-dimethylamino-2-fluorobutyrophenone, M.P. 171° – 174°C;
γ-[4-Hydroxy-4-(3-trifluoromethylphenyl)piperidin-1-yl]-2-dimethylamino-4-fluorobutyrophenone, M.P. 92° – 93°C;
γ-[4-Hydroxy-4-(3-trifluoromethylphenyl)piperidin-1-yl]-4-dimethylamino-2-fluorobutyrophenone, IR 1660 cm$^{-1}$ (C=O), etc.

EXAMPLE 11

A mixture of γ-[4-(4-chlorophenyl)-4-hydroxypiperidin-1-yl]-2,4-difluorobutyrophenone (1.5 g), piperidine (15.0 g) and toluene (50 ml) was heated for 23 hours under refluxing. The reaction mixture was diluted with water and extracted with toluene. The extract was sufficiently washed with water, dried over anhydrous sodium sulfate and concentrated under reduced pressure. The residue was treated with hydrochloric acid in ethanol-ether, and the resulting product was recrystallized from isopropanol to yield γ-[4-(4-chlorophenyl)-4-hydroxypiperidin-1-yl]-4-fluoro-2-piperidinobutyrophenone hydrochloride. M.P 218° – 220°C (decomposition).

EXAMPLE 12

A mixture of γ-[4-(4-chlorophenyl)-4-hydroxypiperidin-1-yl]-2,4-difluorobutyrophenone (3.94 g), 4-(p-chlorophenyl)-4-hydroxypiperidine (2.24 g) and dimethylsulfoxide (30 ml) was stirred at room temperature for 14 hours. The mixture was poured into 300 ml of water and extracted with ethyl acetate. The extract was washed with water, dried over anhydrous sodium sulfate and concentrated under reduced pressure. The residue was recrystallized from ethanol to yield γ,4-bis-[4-(4-chlorophenyl)-4-hydroxypiperidin-1-yl]-2-fluorobutyrophenone. M.P. 190° – 193°C.

EXAMPLE 13

In the same manner as in Examples 11 and 12, the following compounds were obtained:
γ-[4-(4-Chlorophenyl)-4-hydroxypiperidin-1-yl]-2-fluoro-4-(4-oxo-1-phenyl-1,3,8-triazaspiro[4,5]decan-8-yl)butyrophenone, M.P. 197° – 200°C;
γ-[4-Hydroxy-4-(3-trifluoromethylphenyl)piperidin-1-yl]-2-fluoro-4-(4-phenylpiperazin-1-yl)butyrophenone, etc.

EXAMPLE 14

A mixture of γ-[4-hydroxy-4-(3-trifluoromethylphenyl)piperidin-1-yl]-2-benzylamino-4-fluorobutyrophenone (3.8 g), 10 % palladium on charcoal (1.0 g) and 35 % hydrochloric acid (2.0 g) in ethanol (45 ml) was vigorously stirred in hydrogen atmosphere at 25°C until an equimolar amount of hydrogen was consumed. The catalyst was filtered off, and the filtrate was concentrated under reduced pressure to afford γ-[4-hydroxy-4-(3-trifluoromethylphenyl)piperidin-1-yl]-2-amino-4-fluorobutyrophenon hydrochloride. M.P. 230° – 235°C (decomposition). The hydrochloride was shaken with a mixture of aqueous ammonia and ether. The ethereal layer was washed with water, dried over anhydrous sodium sulfate and concentrated under reduced pressure to yield the free base, which was recyrstallized from aqueous ethanol. M.P. 105° – 107°C.

EXAMPLE 15

In the same manner as in Example 14, the following compounds were obtained:
γ-[4-(4-Chlorophenyl)-4-hydroxypiperidin-1-yl]-2-amino-4-fluorobutyrophenone, M.P. 145° – 147°C; hydrochloride, M.P. 236°C (decomposition);
γ-(4-Oxo-1-phenyl-1,3,8-triazaspiro[4,5]decan-8-yl)-2-amino-4-fluorobutyrophenone;
γ-[4-(2-Oxo-1-benzimidazolinyl)piperidin-1-yl]-2-amino-4-fluorobutyrophenone;
γ-[4-(2-Methoxyphenyl)piperazin-1-yl]-2-amino-4-fluorobutyrophenone;
γ-(1,2,3,4-Tetrahydroisoquinolin-2-yl)-2-amino-4-fluorobutyrophenone;

γ-[4-Hydroxy-4-(3-trifluoromethylphenyl)piperidin-1-yl]-4-amino-2-fluorobutyrophenone, etc.

What is claimed is:

1. A process for producing butyrophenone derivatives and their acid addition salts, which comprises reacting a compound of the formula:

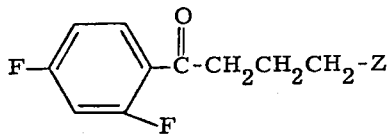

with a secondary amine of the formula:

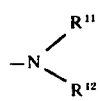

wherein $R^{11}$ and $R^{12}$ are each hydrogen, $C_1$-$C_8$ alkyl, hydroxy-substituted $C_1$-$C_8$ alkyl, $C_1$-$C_4$ alkoxy substituted $C_1$-$C_8$ alkyl, di($C_1$-$C_4$ alkyl) amino-substituted $C_1$-$C_8$ alkyl, $C_3$-$C_7$ cycloalkyl or optionally substituted aralkyl, at least one of $R^{11}$ and $R^{12}$ being an optionally substituted benzyl group, to give an intermediate compound of the formula:

wherein Ar is a group of either one of the formulas:

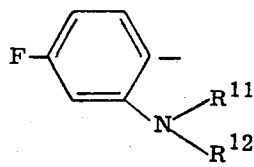 and 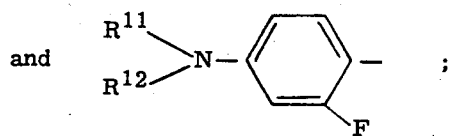 ;

Z is a secondary amino group of either one of the formulas:

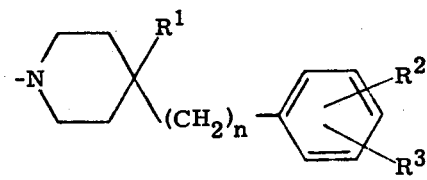

wherein $R^1$ is hydrogen or hydroxyl, $R^2$ and $R^3$ are each hydrogen, halogen, $C_1$-$C_4$ alkyl, $C_1$-$C_4$ alkoxy or trifluoromethyl and n is a integer of 0 or 1;

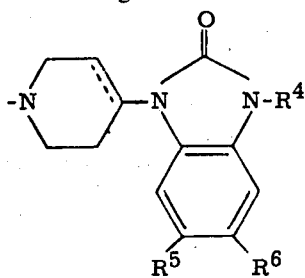

wherein $R^4$ is hydrogen or $C_1$-$C_4$ alkyl, $R^5$ and $R^6$ are each hydrogen, halogen or $C_1$-$C_4$ alkyl and the dotted line is an optional bond between the carbon atoms at the 3- and 4-positions of the piperidine ring,

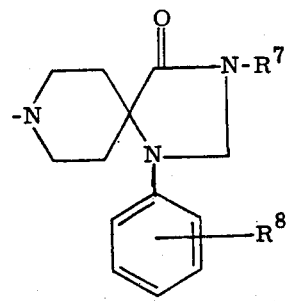

wherein $R^7$ is hydrogen or $C_1$-$C_4$ alkyl and $R^8$ is hydrogen, halogen, $C_1$-$C_4$ or $C_1$-$C_4$ alkoxy,

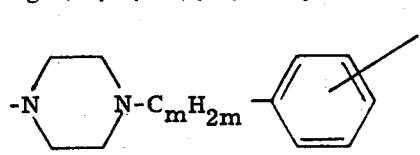

wherein $R^9$ is hydrogen, halogen, $C_1$-$C_4$ alkyl, $C_1$-$C_4$ alkoxy or trifluoromethyl and m is an integer of 0, 1 or 2, and

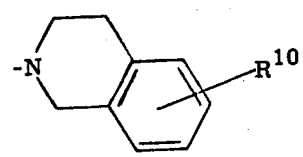

wherein $R^{10}$ is hydrogen, halogen, hydroxyl, $C_1$-$C_4$ alkyl or $C_1$-$C_4$ alkoxy; and thereafter hydrogenating said intermediate compound to give the corresponding compound wherein the optionally substituted benzyl group is eliminated.

2. The process according to claim 1, wherein said optionally substituted benzyl group is selected from the group consisting of unsubstituted benzyl or substituted benzyl substituted with methoxy, methyl, fluoro or chloro.

3. The process according to claim 2, wherein said optionally substituted benzyl group is selected from the group consisting of benzyl, p-methoxybenzyl, p-methylbenzyl, o,p-dimethylbenzyl, p-fluorobenzyl, p-chlorobenzyl, α-ethylbenzyl.

4. The process according to claim 1, wherein the optionally substituted aralkyl groups are selected from the group consisting of phenethyl, benzhydryl, naphthalenemethyl, unsubstituted phenethyl, substituted phenethyl substituted with hydroxy, unsubstituted benzyl and substituted benzyl substituted with methoxy, methyl, ethyl, fluoro or chloro.

5. The process according to claim 4, wherein the optionally substituted aralkyl groups are selected from the group consisting of benzyl, p-methoxybenzyl, methylbenzyl, o,p-dimethylbenzyl, p-fluorobenzyl, p-chlorobenzyl, α-ethylbenzyl, phenethyl, 3,4-dihydroxyphenethyl, benzhydryl, and 1-naphthalenemethyl.

6. The process according to claim 4, wherein said nonpolar solvent is selected from the group consisting of benzene, toluene, xylene, dioxane and carbon tetrachloride.

* * * * *